US005547942A

United States Patent [19]
Rapaport

[11] Patent Number: 5,547,942
[45] Date of Patent: Aug. 20, 1996

[54] METHOD OF TREATMENT OF DIABETES MELLITUS BY ADMINISTRATION OF ADENOSINE 5'-TRIPHOSPHATE AND OTHER ADENINE NUCLEOTIDES

[76] Inventor: Eliezer Rapaport, 142 Payson Rd., Belmont, Mass. 02178

[21] Appl. No.: 177,771

[22] Filed: Jan. 4, 1994

[51] Int. Cl.$^6$ .......................... A61K 31/70; C07H 19/167
[52] U.S. Cl. ................................. 514/47; 514/46
[58] Field of Search ................... 514/46, 47; 536/26.13, 536/26.23, 26.26

[56] References Cited

U.S. PATENT DOCUMENTS

| | | | |
|---|---|---|---|
| 4,673,563 | 6/1987 | Berne et al. | 514/46 |
| 5,104,859 | 4/1992 | Sollevi | 514/46 |
| 5,187,162 | 2/1993 | Marangos | 514/46 |
| 5,227,371 | 7/1993 | Rapaport | 514/46 |
| 5,231,086 | 7/1993 | Sollevi | 514/46 |
| 5,236,908 | 8/1993 | Gruber et al. | 514/46 |
| 5,284,834 | 2/1984 | Jacobson et al. | 514/46 |

OTHER PUBLICATIONS

Loubatieres–Mariani et al. Eur. J. Pharmacol. 59:277–286, 1979.

*Primary Examiner*—Gary L. Kunz
*Attorney, Agent, or Firm*—Pollock, Vande Sande & Priddy

[57] ABSTRACT

The administration of adenine nucleotides or adenosine and inorganic phosphate to a human patient results in the generation of elevated liver, other organs and red blood cell adenosine 5'-triphosphate (ATP) pools as well as increased levels of ATP in the extracellular blood plasma compartment of the blood. The present invention deals with the utilization of the elevated extracellular levels of ATP for achieving the well-established stimulation of insulin secretion following the interactions of extracellular ATP pools with pancreatic β cell purine receptors. The invention is therefore concerned with the treatment of patients suffering from non-insulin-dependent diabetes mellitus (NIDDM or Type-II diabetes) and their chronic clinical complications which are the result of continuous hyperglycemia, by the administration of these physiological agents.

26 Claims, No Drawings

5,547,942

METHOD OF TREATMENT OF DIABETES MELLITUS BY ADMINISTRATION OF ADENOSINE 5'-TRIPHOSPHATE AND OTHER ADENINE NUCLEOTIDES

TECHNICAL FIELD

The present invention is concerned with the treatment of humans suffering from non-insulin-dependent diabetes mellitus (NIDDM or Type-II diabetes) with adenosine 5'-triphosphate (ATP) or other adenine nucleotides, yielding elevated blood and blood plasma levels of ATP which in turn stimulate the well-established insulin secretion from pancreatic β cells, resulting in marked improvements in glucose tolerance.

BACKGROUND ART

Insulin is a peptide synthesized, stored and secreted by the β cells present in the pancreatic islets of Langerhans [Orci, L. The insulin cell: its cellular environment and how it processes (pro) insulin. *Diabetes Metab. Rev.* 2:71–106, 1986]. Insulin is a hormone with a wide array of biological activities primarily targeted at the liver, muscle and fat tissues. Through its interaction with cellular receptors, insulin activates systems involved in the intracellular utilization and storage of glucose, amino acids and fatty acids, as well as inhibiting catabolic processes that result in the breakdown of glycogen, protein and fat (Kahn, C. R. and White, M. F. The insulin receptor and the molecular mechanism of insulin action. *J. Clin. Invest.* 82:1151–1156, 1988). Under normal physiological conditions the presence of elevated levels of glucose in the blood leads to insulin secretion in a highly regulated process. Although glucose is the principal stimulus of insulin secretion in humans, its ingestion as part of the food components induces the release of other gastrointestinal hormones that also participate in the promotion of insulin secretion (Meglasson, M. D. and Matschinsky, F. M. Pancreatic islet glucose metabolism and regulation of insulin secretion. *Diabetes Metab. Rev.* 2:163–214, 1986). Blood glucose, however, is sufficient for the induction of insulin secretion in two phases—a short-lived, rapid 1 to 2 minutes first phase, and a longer phase of a delayed onset. The mechanism of insulin release by glucose is not fully understood, but is known to require the entry of glucose into pancreatic β cells and a metabolism within these cells (see Meglasson and Matschinsky, 1986, supra).

Diabetes mellitus is a complex set of diseases that are characterized by high blood glucose levels (hyperglycemia) and altered carbohydrate, lipid and protein metabolism leading to clinical complications from vascular disorders, eye disorders such as retinopathy, glaucoma and cataracts, nephropathy, diabetic neuropathy and a variety of infections. In addition, several serious acute diabetic complications such as diabetic ketoacidosis and lactic acidosis can occur, and often with lethal consequences—especially in the elderly (Pirart, J. Diabetes mellitus and its degeneration complications: prospective study of 4,400 patients observed between 1947 and 1973. *Diabetes Care* 1:168–188, 1978). Most patients can be clinically classified as having either insulin-dependent diabetes mellitus (IDDM or Type-I diabetes) or non-insulin-dependent diabetes mellitus (NIDDM or Type-II diabetes). Diabetes mellitus, or glucose intolerance (GIT), is one of the major diseases in the United States, afflicting mostly the elderly population (it is estimated that 7% of men and 9% of women over the age of 65 years have diabetes mellitus). In the United States about 90% of diabetic patients have Type-II diabetes and most of the remainder suffer from Type-I diabetes. There is evidence that Type-I diabetes is an autoimmune type disease of the pancreatic β cells with a continuous destruction of pancreatic β cells and increased inability to synthesize and secrete insulin (Srikanta, S. et al. Type-I diabetes mellitus in monozygotic twins: chronic progressive β cell dysfunction. *Ann. Intern. Med.* 99:320–326, 1983). In Type-II diabetes there is no significant loss of β cells from pancreatic islets, and although the β cells retain their ability to synthesize and secrete insulin their ability to respond to a glucose challenge is diminished, especially through the first phase of insulin secretion (Genuth, S. Plasma insulin and glucose profiles in normal, obese, and diabetic persons. *Ann. Intern. Med.* 79:812–822, 1973; Leahy, J. L. et al. Chronic hyperglycemia is associated with impaired glucose influence on insulin secretion: a study in normal rats using chronic in vivo glucose infusions. *J. Clin. Invest.* 77:908–915, 1987).

Insulin is the mainstay treatment for essentially all Type-I and many Type-II diabetic patients. Elevated blood levels of insulin produce immediate inhibition of liver glucose production (by glycogenolysis and gluconeogenesis) and a marked stimulation of uptake and metabolism of glucose by muscle and adipose tissue, leading to the overall reduction in blood glucose levels. Insulin treatment is classified into short, intermediate or long acting, depending on the preparation of insulin and its mode of delivery (intravenous vs. intramuscular vs. subcutaneous injections). Many Type-II diabetic patients can be adequately treated by diet or hypoglycemic agents other than insulin. The overwhelming adverse reaction to insulin is hypoglycemia. Hypoglycemia (or low blood glucose) is a major risk and it should be weighed against the benefits of insulin treatment, especially in Type-II diabetes patients where increased plasma insulin can be achieved by proper diet or milder hypoglycemic drugs, since the pancreatic β cells are still capable of secreting insulin in this disease. The oral hypoglycemic agents that are suitable for Type-II diabetic patients are divided into the sulfonylureas and biguanides as well as other oral hypoglycemic agents that are not structurally related. For recent reviews of current antidiabetic drugs, see: Krall, L. P. Oral hypoglycemic agents. In Joslin's *Diabetes Mellitus*, 12th Ed. (Marble, A., et al., Editors) Lea & Febiger, Philadelphia, 1985, pp 412–452; and Kahn, C. R. and Shechter, Y. Insulin, oral hypoglycemic agents, and the pharmacology of the endocrine pancreas. In Goodman & Gilman's *The Pharmacological Basis of Therapeutics*, 8th Ed. (Gilman, A. G. et al., Editors), Pergamon Press, Inc., 1990, pp 1463–1495. Since many diabetic patients, in particular the elderly, suffer from impaired hepatic and renal functions, their ability to metabolize and excrete the synthetic hypoglycemic agents is severely limited, leading to serious adverse reactions.

More than 10 years ago, two studies clearly demonstrated that extracellular ATP and certain analogues of ATP can induce insulin secretion from isolated perfused animal pancreas (Loubatières-Mariani, M. M, Chapal, J., Lignon, F. and Valett, G. Structural specificity of nucleotides for insulin secretory action from the isolated perfused rat pancreas. *Eur. J. Pharmacol.* 59:277–286, 1979; and Chapal, J. and Loubatières-Mariani, M. M. Effects of phosphate-modified adenine nucleotide analogues on insulin secretion from perfused rat pancreas. *Br. J. Pharmacol.* 73:105–110, 1981). More recently it has been shown that insulin secretion can be stimulated by the interaction of $P_{2y}$-purine receptor agonists with the $P_{2y}$-purine receptors present on the surface of pancreatic cells and that synthetic agonists such as adenosine-5'-0-(2-thiodiphosphate) are one hundred times more active than ATP in stimulating insulin secretion in vitro in perfused rat pancreas (Bertrand, G. et al. Adenosine-5'-0-(2-thiodiphosphate) is a potent agonist of $P_2$-purinoceptors mediating insulin secretion from perfused rat pancreas. *Br. J. Pharmacol.* 102:627–630, 1991). The same $P_{2y}$-purine receptor agonist was very recently shown to be effective in stimulating insulin secretion and improving glucose tolerance in rats and dogs in vivo (Hilliare-Buys, D. et al. Stimulation of insulin secretion and improvement of glucose tolerance in rat and dog by the $P_{2y}$-purinoceptor agonist, adenosine 5'-0-(2-thiodiphosphate). *Br. J. Pharmacol.* 109:183–187, 1993). Thus, the purine receptor agonists that were selected for the studies of stimulation of insulin secretion by pancreatic cells in vitro or in vivo are analogues of ATP such as 2-methylthio ATP, which is a much more powerful agonist for the $P_{2y}$ receptor than is ATP (Ribes, G. et al. Effects of 2-methylthio ATP on insulin secretion in the dog in vivo. *Eur. J. Pharmacol.* 155:171–174, 1988) or analogues of ATP that are both stronger agonists with increased chemical and biological stability, such as adenosine 5'-0-(2-thiodiphosphate) (Bertrand, G. et al., 1991, supra; Hilliare-Buys, D. et al., 1993 supra). These recent reports rule out ATP itself as a potential agent for the stimulation of insulin secretion for the stated reasons: in vivo instability due to rapid metabolism and poor agonist properties for the $P_{2y}$-purine receptor.

U. S. Pat. No. 4,880,918 entitled "Arrest and Killing of Tumor Cells by Adenosine 5'-Diphosphate and Adenosine 5'-Triphosphate" to Rapaport, U.S. Pat. No. 5,049,372 entitled "Anticancer Activities in a Host by Increasing Blood and Plasma Adenosine 5'-Triphosphate (ATP) Levels" to Rapaport, and U.S. Pat. No. 5,227,371 entitled "Utilization of Adenine Nucleotides and/or Adenosine and Inorganic Phosphate for Elevation of Liver, Blood and Blood Plasma Adenosine 5'-Triphosphate Concentrations" to Rapaport, disclose the treatment of cancer by administration of adenine nucleotides to a human host and/or disclose a method to expand organ, blood and blood plasma ATP pools by the administration of adenine nucleotides and/or adenosine and inorganic phosphate to a human host.

The role of intracellular ATP as a cellular energy source, a phosphate group donor for phosphorylation reactions and an allosteric regulator of the activities of a variety of cellular proteins has been well-established. Only in the past 10 years have the roles of adenosine and ATP began to emerge as powerful physiological extracellular modulators of intravascular, extravascular and CNS functions, a role which is attracting significant attention within the field of drug development (Williams, M. Purinergic drugs: opportunities in the 1990's. *Drug Devel. Res.* 28:438–444, 1993). Adenosine is the endogenous ligand for the A (or $P_1$) type purine receptors affecting mostly cardiovascular and CNS functions, whereas ATP is the ligand for $P_2$ type purine receptors and is now an accepted neurotransmitter (Benham, C. D. ATP joins the fast lane. *Nature* 359:103–104, 1992; Edwards, F. A., Gibb, A. J. and Colquhoun, D. ATP receptor-mediated synaptic currents in the central nervous system. *Nature* 359:144–147, 1992).

The administration of adenine nucleotides (e.g., ATP, AMP or other adenine nucleotides) into the systemic circulation results in the immediate degradation of the nucleotide to adenosine and inorganic phosphate. This degradation in the vascular bed is followed by incorporation of the adenosine and inorganic phosphate into liver ATP pools (steady state levels) yielding significant expansion of the liver ATP pools, which is followed by an expansion of red blood cell ATP pools. The red blood cells with expanded ATP pools which are produced by this mechanism slowly release micromolar levels of ATP into the blood plasma without undergoing hemolysis, thus achieving elevated steady state extracellular ATP levels, in spite of the catabolic enzymatic activities present intravascularly (Rapaport, E. and Fontaine, J. Anticancer activities of adenine nucleotides in mice are mediated through the expansion of erythrocyte ATP pools. *Proc. Natl. Acad. Sci. USA* 86:1662–1666, 1989). These elevated levels of ATP inhibit both tumor growth and host weight loss in tumor-bearing murine models. The inhibition of tumor growth proceeds by the receptor-mediated and non-receptor-mediated effects of extracellular ATP on the tumor cell membrane, whereas the inhibition of host weight loss in tumor-bearing hosts is the result of ATP-mediated marked slowdown of hepatic gluconeogenesis and reversal of the depletion of visceral energy stores (Rapaport, E. Mechanisms of anticancer activities of adenine nucleotides in tumor-bearing hosts. *Ann. NY Acad. Sci.* 603:142–150, 1990).

Administration of ATP by intravenous infusions at a dose of 50 µg/kg min for at least 48 hours yielded a doubling of blood (red blood cell) ATP levels after 24 hours in advanced cancer patients (most of whom were at stage IIIB or IV non-small cell lung cancer). Hyperuricemia developed only after at least 48 hours of continuous infusions (Haskell, C. M. and Sanchez-Anaya, D. Hyperuricemia as a complication of ATP: preliminary observation of a phase I clinical trial. *ASCO Proc.* 12:435A, 1993)and could be easily dealt with by administering allopurinol. The elevated blood ATP levels declined within several days after termination of the ATP infusions with a return of total blood ATP levels to their basal levels. In advanced cancer patients with cachexia and malnutrition, the basal blood ATP levels were lower than normal but could be elevated to well above a normal level after ATP infusions.

The mechanisms of expansion of organ ATP levels after administration of ATP proceed by both the increased supply of the major purine precursor for salvage ATP synthesis in cells (adenosine), and by the interaction of extracellular ATP with membrane $P_2$-purine receptors which signals an enhanced intracellular ATP synthesis. Most of the expansions of total blood (red blood cell) ATP pools occur due to increased supply of purines to the mature erythrocyte in the hepatic sinusoids, where these purine precursors (mostly adenosine) arise from the increases in turnover of hepatic ATP pools (Rapaport, E. and Fontaine, J. Generation of extracellular ATP in blood and its mediated inhibition of host weight loss in tumor-bearing mice. *Biochem. Pharmacol.* 38:4261–4266, 1989). A significant increase in red blood cell ATP pools of the magnitude observed in vivo after ATP administration cannot be obtained in vitro (Rapaport, E. and Fontaine, J. Anticancer activities of adenine nucleotides in mice are mediated through expansion of erythrocyte ATP pools. *Proc. Natl. Acad. Sci. USA* 86:1662–1666, 1989).

Adenosine 5'-triphosphate (ATP) infusions useful against metastatic refractory cancers are in phase I of human clinical trials. The two questions which are being answered by these trials are: 1) is it possible to achieve the degree of elevation of red blood cells and blood plasma compartment pools of ATP after the administration of ATP to patients as was shown extensively in preclinical murine models, and 2) can the elevated ATP levels in the human host produce the spectrum of anticancer activities demonstrated in experimental animals (Rapaport, E. Mechanisms of anticancer activities of adenine nucleotides in tumor-bearing hosts. *Ann. NY Acad. Sci.* 603:142–150, 1990).

A variety of in vitro and in vivo studies have demonstrated several anticancer activities of extracellular (blood plasma compartment) pools of ATP as well as elevated hepatic and red blood cell pools of ATP. These activities are a) cytostatic and cytotoxic effects on the tumor; b) anticachexia effects and improvement in hepatic and renal functions; c) modulation of tumoral blood flow; d) antianemia effects; e) antipain activities; f) improvements in motor functions, performance status; g) improvements in oxygen delivery to peripheral sites; h) enhancement of superoxide anion ($O_2$) production by phagocytic cells, and i) significant antithrombotic effects in vivo. All of these anticancer activities observed either in experimental animals or in humans after the administration of ATP have been reviewed recently (Rapaport, E. Anticancer activities of adenine nucleotides in tumor-bearing hosts. *Drug Devel. Res.* 28:428–431, 1993).

The administration of ATP to tumor-bearing murine hosts was also shown to markedly inhibit host weight loss in a cachectic tumor model and, as importantly, the administration of ATP or other adenine nucleotides was shown to elevate extracellular, blood plasma compartment steady state levels (pools) of ATP. The inhibition of tumor growth and host weight loss were shown not to exhibit a cause and effect relationship in murine models.

Whereas ATP itself has been shown a long time ago to stimulate insulin secretion from the pancreatic β cells of the isolated perfused rat pancreas (Loubatières-Mariani, et al., 1979, supra; Chapal and Loubatières-Mariani, 1981, Supra), extensive studies that followed these initial reports demonstrated that only synthetic analogues of ATP can be considered for stimulating insulin secretion in vivo. These analogues include 2-methylthio ATP, a powerful agonist of the $P_{2y}$-purine receptor which is 45 times more potent than ATP in increasing insulin secretion in in vitro systems (Bertrand, G. et al. Evidence for two different $P_2$-purinoceptors on β cell and pancreatic vascular bed. *Br. J. Pharmacol.* 91:783–787, 1987), and which was demonstrated to be effective in the dog by its direct infusion into the pancreaticoduodenal artery (Ribes, G., 1988, supra). The other (and even more powerful) analogue of ATP is the chemically and biologically stable adenosine-5'-0-(2-thiodiphosphate) which is also a strong $P_{2y}$-purine receptor agonist and was shown to be 100 times more potent than ATP in the in vitro insulin secretion system of the isolated perfused pancreas of the rat (Bertrand, G. et al., 1991, supra). Adenosine-5'-0-(2-thiodiphosphate) was then used successfully in the rat and dog in vivo in an injectable or oral delivery system for stimulation of insulin secretion (Hilliare-Buys, D. et al., 1993, supra). Thus, all the previous data teach away from ATP itself being utilized as an insulin secretagogue in vivo in a human suffering from glucose intolerance. The widely accepted notion is that ATP is a weak $P_{2y}$-purine receptor (the extracellular receptor involved in the regulation of insulin secretion) agonist as compared to other available synthetic ATP analogues. More importantly, the state of the art teaches that because of the rapid degradation of ATP in vivo, only a chemically and biologically stable analogue of ATP would provide a sufficient agonist concentration at the $P_{2y}$-purine receptors of the pancreatic β cells to affect insulin secretion in a therapeutically meaningful way.

SUMMARY OF THE INVENTION

The present invention is concerned with the administration of ATP or other adenine nucleotides or adenosine and inorganic phosphate to a human patient suffering from non-insulin-dependent diabetes mellitus (NIDDM or Type-II diabetes) for the purpose of elevating total blood and blood plasma (extracellular) levels of ATP, which are then sufficient to act on the $P_{2y}$-purine receptors present on pancreatic β cells and stimulate insulin secretion from these cells. The key to the invention is the ability to significantly increase total blood and blood plasma ATP levels in a human patient, which is totally unexpected.

BEST AND VARIOUS MODES FOR CARRYING OUT THE INVENTION

It has been found pursuant to the present invention that a human patient suffering from diabetes mellitus and its clinical complications initiated by the impairment in glucose tolerance can be treated by administering a member selected from the group consisting of: (a) a mixture of adenosine and/or inorganic phosphate; and (b) an adenine nucleotide wherein said adenine nucleotide containing adenosine moiety(ies) and phosphate moiety(ies) and undergoes a rapid degradation to adenosine and inorganic phosphate after administration to said patient.

Examples of such materials are adenosine 5'-monophosphate (AMP), adenosine 5'-diphosphate (ADP), adenosine 5'-triphosphate (ATP) and mixtures of adenosine and an inorganic phosphate.

Examples of inorganic phosphates are sodium phosphate, potassium phosphate and phosphoric acid. The pH of any solution employed containing the phosphate is usually adjusted, if necessary, to about 6.0 to about 7.5 by the addition of a base such as sodium hydroxide. Usually, at least about 1 equivalent of phosphate per adenosine is employed, and preferably about 1 to about 3. In addition, pharmaceutically acceptable salts, or metal complexes, or chelates, or liposomes, or radio-nuclides of the above compounds can be employed.

Preparations containing the above ingredients can be employed in a variety of conventional pharmaceutical preparations. These preparations can contain organic or inorganic material suitable for enteral or parenteral administration. The high solubility of AMP and/or ADP and/or ATP salts and/or adenosine and phosphate salts in isotonic aqueous solutions of sodium chloride enable administration of these agents in the form of injection or infusion of single or multiple doses. The injection or infusion can be intraperitoneal, intravenous, or intraarterial. AMP and/or ADP and/or ATP and/or adenosine and phosphate salts are also suitable for oral, enteral, or topical application when employed with conventional organic or inorganic carrier substances.

The effective doses are in the range of about 0.1–100 mg/kg of body weight per 24 hours for oral or topical administration, and 0.01–10mg/kg of body weight per 24 hours for injections. Intravenous, intraperitoneal, or intraarterial infusions of AMP and/or ADP and/or ATP and/or adenosine and phosphate salts in a suitable salt form are preferably administered at a rate of about 0.001–1mg/kg of body weight per minute. The delivery of these agents can be performed using a wide variety of drug delivery systems including, but not limited to, pumps or liposomes.

Since diabetes mellitus is a major chronic disease afflicting the elderly population, preparations of adenine nucleotides or adenosine and inorganic phosphate that can be delivered orally are particularly desirable. Such preparations include the compounds in the form of a tablet soluble in the intestines or solutions or sol id formulations suitable for sublingual delivery into the systemic circulation. The effective doses suitable for oral or sublingual administration are in the range of 0.1–100 mg/kg of body weight per 24 hours.

Administration of adenosine and inorganic phosphate or adenine nucleotides such as, but not limited to, AMP, ADP, or ATP to a patient suffering from glucose intolerance (GIT) would result in the return of blood glucose levels to their normal values. The mechanisms involved in the regulation of blood sugar levels by the present invention include the rapid expansion of total blood and blood plasma ATP pools, which in turn are sufficient to promote increases in insulin secretion from pancreatic β cells. Because some of the major factors involved in the impairment of glucose tolerance and the development of Type-II diabetes mellitus are related to decreased insulin secretion and increases in insulin degradation and removal, stimulation of insulin secretion by a physiological metabolite such as ATP is a method of choice for improvement of glucose tolerance in the diabetic patient. The use of adenine nucleotides and/or adenosine and inorganic phosphate for the treatment of Type-II diabetes is particularly attractive in comparison with the current use of synthetic non-physiological hypoglycemic drugs. The reason is that in many diabetic patients, especially the elderly, hepatic and renal functions are impaired resulting in adverse effects due to improper clearance of the drugs from the circulation. Adverse effects include hypoglycemia (including coma) which is the result of longer action due to slow clearance of these hypoglycemic agents (Ferner, R. E. and Neil, H. A. W. Sulfonylureas and hypoglycemia. *Br. Med. J.* 296:949–950, 1988; Seltzer, H. S. Drug induced hypoglycemia. *Endocrin. Metab. Clin. North Am.* 18:163–183, 1989). The present invention discloses a physiological process whereby a normal metabolite (e.g., ATP) increases insulin secretion by pancreatic β cells in accordance with the blood glucose levels, which are the major regulator of insulin secretion by these cells. Thus, once normoglycemia is established, the elevated blood ATP levels are not active in increasing insulin secretion and the danger of hypoglycemia is nonexistent.

The use of the present invention for the management of Type-II diabetes is especially suitable for patients suffering from acute or chronic complications of the disease. The acute problems include clinical complications due to renal or vascular diseases which are in turn the result of chronic hyperglycemia. The chronic complications which afflict mostly the elderly suffering from diabetes mellitus include eye problems, such as cataracts, glaucoma and diabetic retinopathy; a variety of infections, and the major complications of diabetic neuropathy, diabetic nephropathy and peripheral vascular disease.

The data discussed above in conjunction with my years of experience with adenine nucleotides and/or mixtures of adenosine and inorganic phosphates has lead me to assert the following conclusions: administration of adenine nucleotides or adenosine and inorganic phosphate to a patient suffering from diabetes mellitus will result in significant increases in organ and red blood cell ATP pools and as a result of the expanded red blood cell ATP pools, elevated levels of ATP will be produced in the extracellular blood plasma compartment. These elevated extracellular ATP levels are produced due to the continuous release of micromolar amounts of ATP from red blood cells into the blood plasma in a non-hemolytic process in spite of the constant degradation of ATP by enzymatic activities present in the vascular bed. The therapeutic targets that will be achieved by the present invention for the treatment of diabetes mellitus are the improvement of glucose tolerance in the diabetic patient which will in turn positively affect the acute and chronic clinical complications due to diabetes and its associated hyperglycemia.

Having thus described my invention, what I claim as new and desire to secure by Letters Patent is:

1. A method for treating chronic diabetes mellitus or chronic non-insulin-dependent diabetes mellitus (NIDDM or Type-II diabetes) in a human diabetic patient by administering to said patient a member selected from the group consisting of: (a) a mixture of adenosine and inorganic phosphate; and/or (b) an adenine nucleotide wherein said adenine nucleotide contains adenosine moiety(ies) and phosphate moiety(ies) and undergoes rapid degradation to adenosine and inorganic phosphate after administration to said patient.

2. The method of claim 1 wherein adenine nucleotides and/or adenosine and inorganic phosphate are administered to a diabetic patient in order to improve glucose tolerance.

3. The method of claim 1 wherein adenine nucleotides and/or adenosine and inorganic phosphate are administered to a diabetic patient in order to treat the chronic complications resulting from hyperglycemia, including vascular disease, disorders in kidney function, eye complications and diabetic neuropathy.

4. The method of claim 1 wherein adenine nucleotides are administered to a patient as pharmaceutically acceptable salts thereof, chelates thereof, or metal complexes thereof, or liposomes thereof.

5. The method of claim 1 wherein the amount of adenosine is about 0.001–1 mg/kg of body weight per minute and said administration is by infusion.

6. The method of claim 1 wherein the amount of adenosine is about 0.01–10 mg/kg of body weight per 24 hours and said administration is by injection.

7. The method of claim 1 wherein the amount of adenosine is about 0.1–100 mg/kg of body weight per 24 hours and said administration is oral, sublingual, or topical.

8. The method of claim 1 wherein the amount of adenine nucleotide is about 0.001–1 mg/kg of body weight per minute and said administration is by infusion.

9. The method of claim 1 wherein the amount of adenine nucleotide is about 0.01–10 mg/kg of body weight per 24 hours and said administration is by injection.

10. The method of claim 1 wherein the amount of adenine nucleotide is about 0.1–100 mg/kg of body weight per 24 hours and said administration is oral, sublingual, or topical.

11. The method of claim 1 wherein adenosine and inorganic phosphate are administered to said patient.

12. The method of claim 1 wherein adenosine 5'-monophosphate is administered to said patient.

13. The method of claim 1 wherein adenosine 5'-triphosphate is administered to said patient.

14. The method of claim 1 wherein a mixture of inorganic phosphate and adenosine is administered to said patient and wherein said inorganic phosphate is selected from the group consisting of sodium phosphate, potassium phosphate and phosphoric acid.

15. The method of claim 1 wherein said phosphate employed is an aqueous solution having a pH of about 6.0 to about 7.5.

16. The method of claim 1 wherein at least about 1 equivalent of phosphate per equivalent of adenosine is employed.

17. The method of claim 1 wherein the molar ratio of adenosine to inorganic phosphate is about 1:1 to about 1:3.

18. The method of claim 1 wherein said member is in the form of a pharmaceutically acceptable salt.

19. A process for treating chronic non-insulin-dependent diabetes mellitus (NIDDM or Type II diabetes) in a human diabetic patient by administering an adenine nucleotide and/or mixture of adenosine and inorganic phosphate to said patient for the purpose of elevating tissue, total blood and blood plasma levels of ATP sufficient to increase insulin secretion by pancreatic β cells and achieve physiological control of blood plasma glucose levels.

20. The process of claim 19 wherein said treating is with at least one compound selected from the group of adenosine and inorganic phosphate, adenosine 5'monophosphate, adenosine 5'-diphosphate, adenosine 5'-triphosphate, pharmaceutically acceptable salts thereof or chelates thereof.

21. The process of claim 19 wherein said treating is with adenosine and inorganic phosphate.

22. The process of claim 19 wherein said treating is with adenosine 5'-monophosphate.

23. The process of claim 19 wherein said treating is with adenosine 5'-triphosphate.

24. The process of claim 20 wherein the amount of said compound is a dose of about 0.001–1 mg/kg of body weight of said host per minute and said administering is by infusion.

25. The process of claim 20 wherein the amount of said compound is a dose of about 0.01–10 mg/kg of body weight of said host per 24 hours and said administering is by injection.

26. The process of claim 20 wherein the amount of said compound is a dose of about 0.1–100 mg/kg of body weight of said host per 24 hours and said administering is oral or topical.

* * * * *